United States Patent
Haghiri-Gosnet et al.

(10) Patent No.: US 10,393,699 B2
(45) Date of Patent: Aug. 27, 2019

(54) MICROFLUIDIC ANALYSIS DEVICE AND METHOD

(71) Applicants: CENTRE NATIONAL DE LA RECHERCHE SCIENTIFIQUE (CNRS), Paris (FR); UNIVERSITE PARIS-SUD, Orsay (FR)

(72) Inventors: Anne-Marie Haghiri-Gosnet, Sceaux (FR); Antoine Pallandre, Sceaux (FR); Jean Gamby, Saint Ouen (FR); Daniel Rose, Everly (FR); Sebastien Meance, Toulouse (FR)

(73) Assignees: CENTRE NATIONAL DE LA RECHERCHE SCIENTIFIQUE (CNRS), Paris (FR); UNIVERSITE PARIS—SUD, Orsay (FR)

( * ) Notice: Subject to any disclaimer, the term of this patent is extended or adjusted under 35 U.S.C. 154(b) by 51 days.

(21) Appl. No.: 15/508,069

(22) PCT Filed: Sep. 4, 2015

(86) PCT No.: PCT/EP2015/070211
§ 371 (c)(1),
(2) Date: Mar. 1, 2017

(87) PCT Pub. No.: WO2016/034696
PCT Pub. Date: Mar. 10, 2016

(65) Prior Publication Data
US 2017/0284961 A1    Oct. 5, 2017

(30) Foreign Application Priority Data
Sep. 5, 2014   (FR) ...................... 14 58333

(51) Int. Cl.
G01N 27/447   (2006.01)
B01L 3/00   (2006.01)
G01N 30/28   (2006.01)

(52) U.S. Cl.
CPC .... G01N 27/44752 (2013.01); B01L 3/50273 (2013.01); B01L 3/502715 (2013.01);
(Continued)

(58) Field of Classification Search
CPC ....... G01N 27/44752; G01N 27/44791; G01N 2030/285; B01L 3/502753;
(Continued)

(56) References Cited

U.S. PATENT DOCUMENTS

| 5,092,972 A | 3/1992 | Ghowsi |
| 5,320,730 A | 6/1994 | Ewing et al. |
| 2011/0272281 A1* | 11/2011 | Plecis .............. G01N 27/44752 204/451 |

FOREIGN PATENT DOCUMENTS

| WO | WO 0028315 A1 | 5/2000 |
| WO | WO 2010057387 A1 | 5/2010 |

OTHER PUBLICATIONS

International Search Report and Written Opinion in PCT/EP2015/070211 dated Nov. 18, 2015, with English translation.
(Continued)

*Primary Examiner* — J. Christopher Ball
(74) *Attorney, Agent, or Firm* — Womble Bond Dickinson (US) LLP (57) ABSTRACT

The present invention relates to a microfluidic analysis device (1) including: a substrate (20) wherein a separation channel (10) is arranged, in which an electrolyte flows, a portion of the separation channel (10) being covered with a polarizable surface (11); two longitudinal field electrodes (8a, 8b) arranged on either side of the separation channel
(Continued)

(10); at least one control electrode (6a, 6b) positioned in the separation channel (10), the control electrode (6a, 6b) being suitable for polarizing the polarizable surface (11) so as to control the speed of the electro-osmotic flow in the separation channel (10); the microfluidic analysis device (1) being characterised in that the polarizable surface (11) includes an insulating sub-layer (12) made of amorphous silicon carbide (SiC) and an upper polarizable layer (13) in direct contact with the electrolyte, the control electrodes (6a, 6b) being positioned between the insulating sub-layer (12) and the upper polarizable layer (13).

10 Claims, 5 Drawing Sheets

(52) U.S. Cl.
CPC ... *B01L 3/502746* (2013.01); *B01L 3/502753* (2013.01); *G01N 27/44791* (2013.01); *B01L 2200/143* (2013.01); *B01L 2300/0645* (2013.01); *B01L 2300/0816* (2013.01); *B01L 2300/16* (2013.01); *B01L 2400/0418* (2013.01); *B01L 2400/0421* (2013.01); *G01N 2030/285* (2013.01)

(58) Field of Classification Search
CPC ......... B01L 3/502715; B01L 3/502746; B01L 3/50273; B01L 2200/143; B01L 2300/16; B01L 2300/0816; B01L 2300/0645; B01L 2400/0418; B01L 2400/0421
See application file for complete search history.

(56) References Cited

OTHER PUBLICATIONS

Search Report in French Application No. 1458333 dated May 13, 2015, with English translation coversheet.

* cited by examiner

MICROFLUIDIC ANALYSIS DEVICE AND METHOD

FIELD OF THE INVENTION

The invention relates to the field of microfluidic analysis devices making use of the competition of electrophoretic and electro-osmotic mobilities.

STATE OF THE ART

Microfluidic analysis devices adapted to sort particles and molecules are known by making use of the competition of electrophoretic and electro-osmotic mobilities.

These microfluidic analysis devices use a microfluidic array in which an electrolyte and a sample containing analytes are injected.

This array includes a number of tanks connected to at least one long separation channel and/or to a microchannel array having intersections particularly arranged to enable an amount of analytes to be injected in the one separation channel.

The walls of the separation channel are covered with a polarisable surface which consists of a metal layer covered with an insulator. A polarisation voltage is applied to the metal layer so as to modulate the surface charge through the insulator at the interface with the liquid. These devices are commonly called polarisable metal/insulator interface transistors.

The method implemented in these microfluidic analysis devices consists in applying a longitudinal electric field to the channel across longitudinal field electrodes provided on either side of the separation channel. Under the effect of an electric field, charged particles move in the electrolyte. This is called electrophoretic migration or electrophoresis.

On the walls of the separation channel, a double ion layer formed by a fixed ion layer, corresponding to the surface charge, and a mobile ion layer, corresponding to a diffuse layer in the electrolyte, is spontaneously formed. Under the longitudinal electric field, the ions of the mobile layer migrate, causing an overall movement of the electrolyte by electro-osmosis. This is called electro-osmotic flux.

The concomitant action of the electrophoretic migration (related to the charge and size of the molecules or particles in the electrolyte) and the electro-osmotic flux (electrolyte rate) ensures transport of the molecules and particles contained in the electrolyte through the separation channel.

The microfluidic analysis devices of prior art thus enable particles to be separated as a function of their mass and charge.

The microfluidic analysis devices of prior art however have two main drawbacks.

First, because of the insulating layer covering the polarisable surface, a relatively significant potential difference between the electrolyte and the polarisable surface has to be applied to manage a sufficient modulation of the surface charge of the polarisable interface. Applying a significant potential difference between the electrolyte and the polarisable surface triggers electrochemical reactions which generate off-gases likely to deteriorate the polarisable surface.

Secondly, the insulator in contact with the electrolyte is subject to physical degradation which can then give rise to high leakage currents between the polarisable surface and the longitudinal field electrodes, which prevents the surface charge of the polarisable interface to be monitored.

DISCLOSURE OF THE INVENTION

The invention overcomes at least one of the abovementioned drawbacks and enables in particular leakage currents between the polarisable surface and the longitudinal field electrodes to be limited and thus the charge monitoring of the polarisable surface to be improved.

To that end, the invention provides a microfluidic analysis device including:
- a substrate wherein a separation channel is arranged, in which an electrolyte flows, a portion of the separation channel (10) being covered with a polarisable surface (11);
- two longitudinal field electrodes arranged on either side of the separation channel;
- at least one control electrode positioned in the separation channel, the control electrodes being adapted to polarise the polarisable surface so as to monitor the rate of the electro-osmotic flow in the separation channel;

the microfluidic analysis device being characterised in that the polarisable surface includes an insulating sub-layer made of amorphous silicon carbide and an upper polarisable layer in direct contact with the electrolyte, the control electrodes (6a, 6b) being positioned between the insulating sub-layer (12) of amorphous silicon carbide and the upper polarisable layer.

The microfluidic analysis device according to the invention enables the rate of the analytes in the separation channel, or more precisely the electro-osmotic contribution of the transport of particles or molecules, which is directly related to the surface charge of the channel, to be measured.

The invention enables the rate of the analytes flowing in the separation channel to be driven in real time.

The association of the insulating sub-layer of amorphous silicon carbide and the upper polarisable layer enables the potential difference to be applied between the electrolyte and the polarisable surface to be limited in order to generate a modulation of the surface charge of the upper polarisable layer.

The invention thus enables the surface charge to be optimally monitored by avoiding the electrochemical reactions likely to generate off-gases.

Thus, the invention enables the separation or sorting by monitoring the electro-osmotic flux to be optimised by maximising the resolution of the microfluidic analysis method.

The inventors have highlighted that, when the upper polarisable layer is directly deposited onto the glass substrate, as described in document WO 2010/052387, there are leakage currents between the polarisable surface and the longitudinal field electrodes.

Indeed, the upper polarisable layer (in particular when it is of nitrogen carbon CNx and deposited by the sputtering method) is too restrained to directly adhere to the glass. The poor adhesion of the upper polarisable layer to the glass substrate accounts for the existence of these leakage currents between the polarisable surface and the longitudinal field electrodes.

The insulating sub-layer of amorphous silicon carbide by promoting bonding of the upper polarisable layer enables the leakage currents between the polarisable surface and the longitudinal field electrodes to be limited.

Indeed, amorphous silicon carbide is compatible with both the substrate and the upper polarisable layer, which enables two a priori directly incompatible materials to be adhered.

In particular when the substrate is of glass and the upper polarisable layer is of nitrogen carbon, the glass surface is rich in silicon and oxygen whereas the nitrogen carbon CNx contains carbon and nitrogen. The sub-layer of amorphous silicon carbide having common elements with on the one hand the glass substrate and on the other hand the nitrogen carbon CNx, it promotes indirect adhesion of nitrogen carbon CNx to glass.

Further, the inventors have highlighted by atomic force microscopy that the roughness (in particular the RMS (root mean square) roughness) of a surface of amorphous silicon carbide a-SiC and that of a surface of nitrogen carbon CNx are very close to each other and thus that the a-SiC/CNx interface has a very good compatibility in a topographic point of view.

The presence of a sub-layer of amorphous silicon carbide a-SiC, which is a dense electrically insulating amorphous material (the resistivity of the insulating sub-layer of amorphous silicon carbide a-SiC is typically $2 \times 10^3$ Ohms.cm) enables the upper polarisable layer to be polarised while limiting the leakage currents between the polarisable surface and the longitudinal field electrodes. The presence of a sub-layer of amorphous silicon carbide a-SiC typically enables leakage currents to be reduced to less than 1 nanoampere.

The inventors further have observed that if a sub-layer having an electrical conductivity higher than that of CNx, as ITO (indium titanium oxide) and aluminium is used, most of the current passes through the sub-layer, which results in heat generation by Joule effect. A sub-layer of amorphous silicon carbide a-SiC does not have this drawback.

The invention is advantageously completed by the following characteristics, taken along or according to any technically possible combinations.

The upper polarisable layer is of nitrogen carbon CNx.
The microfluidic analysis device further includes:
a reference electrode adapted to measure the potential of the electrolyte in the separation channel;
a monitor circuit adapted to adjust the potential of the control electrode as a function of the electrolyte potential measured by the reference electrode, such that the polarisable surface remains in its polarisability window.

The reference electrode and the monitor circuit enable the leakage currents between the control electrodes and the longitudinal field electrodes to be limited which are detrimental to monitoring and quality of the analyte transport during the electrophoretic migration process.

The monitor circuit is adapted to impose a fixed potential difference between the control electrode and the reference electrode.

The microfluidic analysis device comprises:
one upstream control electrode positioned upstream of the channel;
one downstream control electrode positioned downstream of the channel;
one upstream reference electrode positioned upstream of the channel;
one downstream reference electrode positioned downstream of the channel;
the upstream control electrode is connected by an upstream monitor circuit to the upstream reference electrode, the downstream control electrode being connected by a downstream monitor circuit to the downstream reference electrode, the downstream monitor circuit being adapted to adjust the potential of the control electrodes as a function of the electrolyte potential measured by the reference electrodes, such that the polarisable surface remains in its polarisability window.

The use of the sub-layer of SiC and the monitor circuits together enables leakage currents between the polarisable surface and the longitudinal field electrodes to be limited.

The downstream monitor circuit is connected to a floating ground referenced to the downstream reference electrode.

Measuring the value of the electrolyte potential with respect to the mains ground enables the common mode voltage in the downstream monitor circuit to be limited.

The downstream monitor circuit includes a first operational amplifier, and a second operational amplifier, the downstream reference electrode is connected between the non-inverting input of the first operational amplifier and the floating ground, and the downstream control electrode being connected between the non-inverting input of the second operational amplifier and the floating ground.

The invention also relates to a microfluidic analysis method implemented by a microfluidic analysis device comprising the steps of:
injecting an electrolyte containing analytes into the separation channel;
generating a longitudinal field in the separation channel;
polarising the polarisable surface by applying a polarisation voltage across the control electrodes;
monitoring the electro-osmotic flow rate in the separation channel by modulating the polarisation voltage across the control electrodes.

During the step of monitoring the electro-osmotic flux rate in the separation channel, a fixed potential difference is imposed between the control electrode and the reference electrode.

During the step of monitoring the electro-osmotic flux rate in the separation channel, a fixed potential difference is imposed between the upstream control electrode and the upstream reference electrode, and between the downstream control electrode and the downstream reference electrode.

DESCRIPTION OF THE FIG.

Further purposes, characteristics and advantages will become clearer from the detailed description that follows in reference to the drawings given by way of illustrating and non-limiting purposes in which.

DETAILED DESCRIPTION OF THE INVENTION

Figure 1:
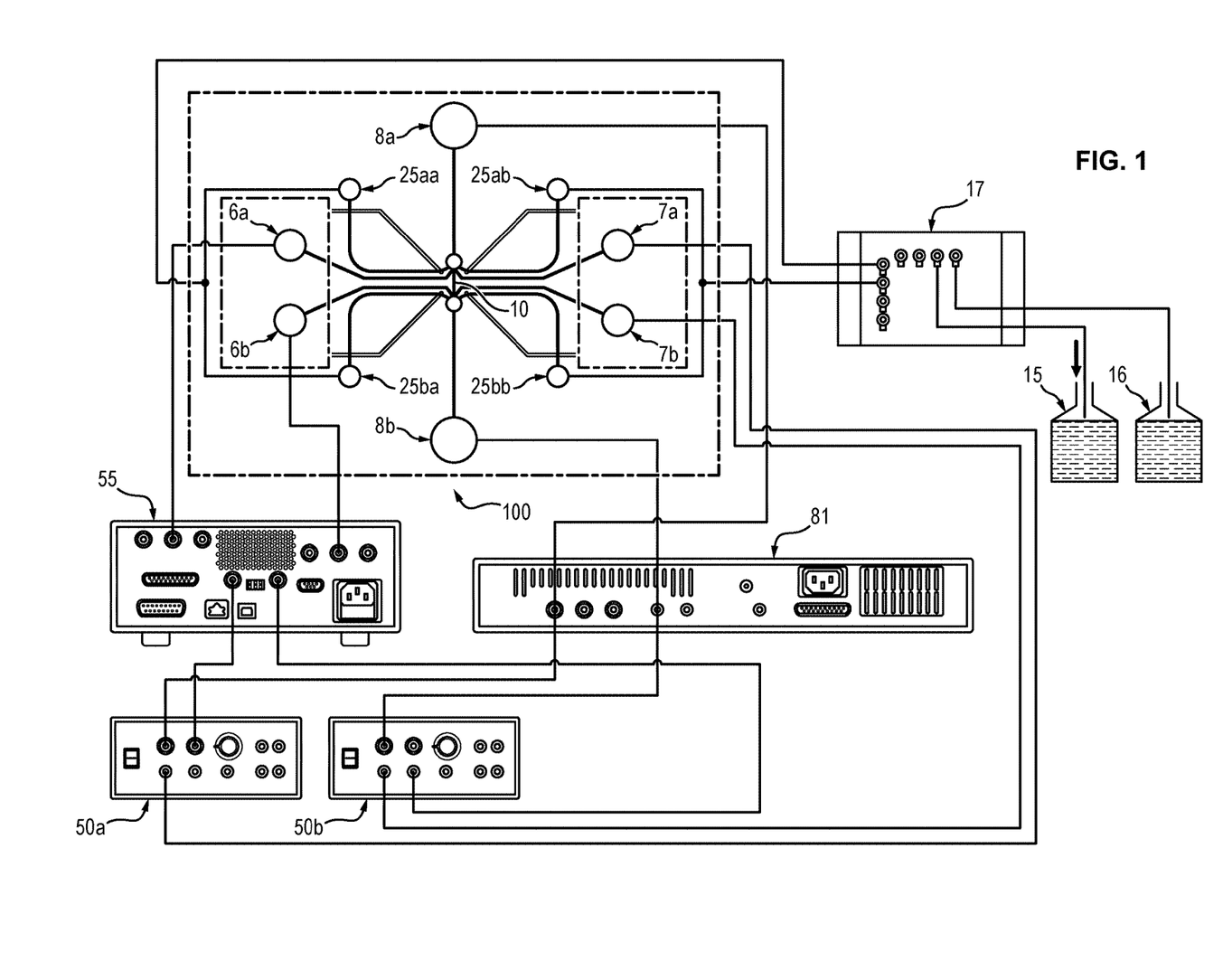
FIG. 1 is a schematic representation of a device in accordance with the invention.
Figure 3:
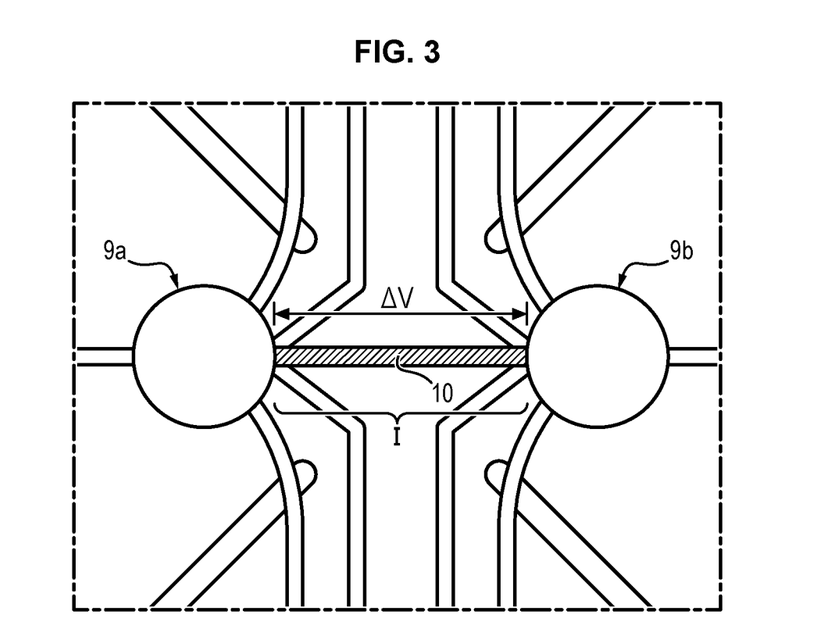
FIG. 3 is a close-up view of the separation channel.

In reference to FIGS. 1 and 3, a microfluidic analysis device 1 comprises a fluidic array 100 made in a substrate 20 of glass or plastic material.

The Fluidic Array 100

The fluidic array 100 includes:
a back-up container 15,
a storage container 16,
a right upstream secondary tank 25*aa*,
a left upstream secondary tank 25*ab*,
a right downstream secondary tank 25*ba*,
a left downstream secondary tank 25*bb*,
an upstream tank 9*a*, a downstream tank 9b,
a separation channel 10.

Air Pressurised Back-Up Container 15 and a Second Storage Container 16

In reference to FIG. 1, the fluidic array 100 includes a back-up container 15 containing an electrolyte containing analytes, and a second storage container 16 adapted to receive the electrolyte at the output of the fluidic array 100.

The electrolyte is for example chloride KCl or any other biological buffer.

The analytes can in particular be:
particles such as micro- or nanometric balls that can be magnetic or not, functionalised chemically or by biomolecules, or by a combination of both;
molecules and chemical elements as biomolecules (DNA, RNA, peptides, proteins), ions, pollutants, polymers, or radioelements; and
bacteria, viruses and cells generally.

The back-up container 15 is pressurised with nitrogen, typically under a pressure in the order of 1 bar.

The back-up container 15 and the storage container 16 are connected to a matrix system of solenoid valves 17 enabling the introduction of the electrolyte into the fluidic array 100 to be controlled, through a hydrodynamic pressure measured by a pressure gauge.

Secondary Tanks 25aa, 25ab, 25ba, 25bb

The back-up container 15 is adapted to be alternately connected on the one hand to the right upstream secondary tank 25aa and to the right downstream secondary tank 25ba and on the other hand to the left upstream secondary tank 25ab and to the left downstream secondary tank 25bb.

The storage container 16 is also adapted to be alternately connected on the one hand to the right upstream secondary tank 25aa and to the right downstream secondary tank 26ba and on the other hand to the left upstream secondary tank 25ab and to the left downstream secondary tank 25bb.

Tanks 9a and 9b

The fluidic array 100 includes an upstream tank 9a and a downstream tank 9b.

The tanks 9a and 9b enable some amount of analytes to be injected into the separation channel 10.

Figure 2:
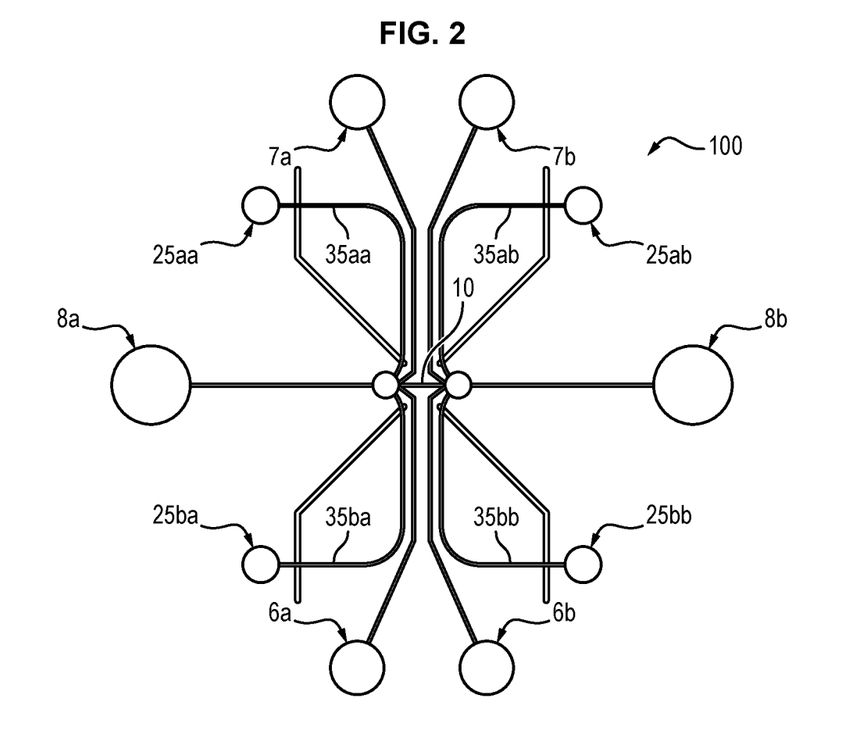
FIG. 2 is a view of the fluidic array of the device of FIG. 1.

The upstream tank 9a is connected to the right upstream secondary tank 25aa and to the left upstream secondary tank 25ba by connecting channels 35aa and 35ba. The downstream tank 9b is connected to the right downstream secondary tank 25ab and to the left downstream secondary tank 25bb by connecting channels 35ab and 35bb.

The connecting channels 35aa, 35ab, 35ba and 35bb have rounded corners and two narrowed sections, so as to limit the presence of air bubbles.

Separation Channel 10

The separation channel 10 connects the upstream longitudinal field tank 9a and the downstream longitudinal field tank 9b.

The separation channel 10 is typically of a rectangular cross-section.

The typical dimensions for the separation channel 10 are 5 000 micrometers long and 250 micrometers wide.

Circuit for Generating a Longitudinal Field in the Separation Channel 10

As illustrated in FIG. 1, the microfluidic measurement device 1 includes a circuit for generating a longitudinal field in the separation channel 10.

The circuit for generating the longitudinal field includes at least one first and one second longitudinal field electrode 8a, 8b powered by a longitudinal electric field voltage generator 81.

The longitudinal electric field generator 81 is current-limited to prevent any current leakage which would degrade the upper polarisable layer 11.

As illustrated in FIG. 3, the longitudinal field electrodes 8a, 8b are each connected to one of the longitudinal field tanks (respectively 9a and 9b) and are able to generate an electric field in the electrolyte.

The longitudinal field electrodes 8a, 8b are for example macroscopic electrodes placed in tanks, or microelectrodes placed in the fluidic array.

Polarisable Surface 11

A part of the separation channel 10 is covered with a polarisable surface 11.

The polarisable surface 11 includes an insulating sub-layer 12 and an upper polarisable layer 13. The upper polarisable layer 13 is in direct contact with the electrolyte.

The insulating sub-layer 12 is of amorphous silicon carbide a-SiC.

The upper polarisable layer 13 is typically of nitrogen carbon CNx.

The insulating sub-layer 12 of SiC has typically a thickness close to 30 nm, whereas the upper polarisable layer 13 has a thickness between 90 nm and 200 nm.

The association of the insulating sub-layer 12 and the upper polarisable layer 13 and in particular the fact that the upper polarisable layer 13 is in direct contact with the electrolyte enables the potential difference which has to be applied between the electrolyte and the polarisable surface 11 to be limited in order to generate a modulation in the surface charge of the upper polarisable layer 11. The invention thus enables the charge surface to be optimally monitored by avoiding the electrochemical reactions likely to generate off-gases.

On the other hand, the insulating sub-layer 12 of amorphous silicon carbide a-SiC promotes bonding of the upper polarisable layer 13.

On the other hand, it plays a perfect insulating rule which contributes to reducing the leakage currents between the polarisable surface and the longitudinal field electrodes. The resistivity of the insulating sub-layer 12 of amorphous silicon carbide a-SiC is typically $2 \times 10^3$ Ohms.cm.

In the presence of the insulating sub-layer 12, the leakage currents between the polarisable surface 11 and the longitudinal field electrodes 8a, 8b are typically lower by a factor of one thousand to currents delivered by the longitudinal field electrodes 8a, 8b. The leakage currents between the polarisable surface 11 and the longitudinal field electrodes 8a, 8b are typically in the order of 5 nanoamperes.

Control Electrodes 6a, 6b

The device comprises one or more control electrodes 6a, 6b adapted to polarise the polarisable surface 11.

The device advantageously comprises at least one upstream control electrode 6a, and one downstream control electrode 6b each connected to one of the ends of the polarisable surface 11.

The upstream control electrode 6a is positioned at the upstream end of the separation channel 10. The downstream control electrode 6b is positioned at the downstream end of the separation channel 10.

The control electrodes 6a, 6b are positioned between the insulating sub-layer 12 and the upper polarisable layer 13.

The control electrodes 6a, 6b are typically of platinum.

Reference Electrodes 7a, 7b

The microfluidic measurement device 1 comprises reference electrodes 7a, 7b adapted to measure the electrolyte potential.

The upstream reference electrode 7a is located upstream of the upper polarisable layer 11 in direct contact with the electrolyte and measures the potential upstream of the polarisable surface 11. The downstream reference electrode 7b is located downstream of the upper polarisable layer 11 in direct contact with the electrolyte and measures the potential downstream of the polarisable surface 11.

The reference electrodes 7a, 7b are typically of platinum or AgCl.

Monitor Circuit 50a and 50b

Figure 4:
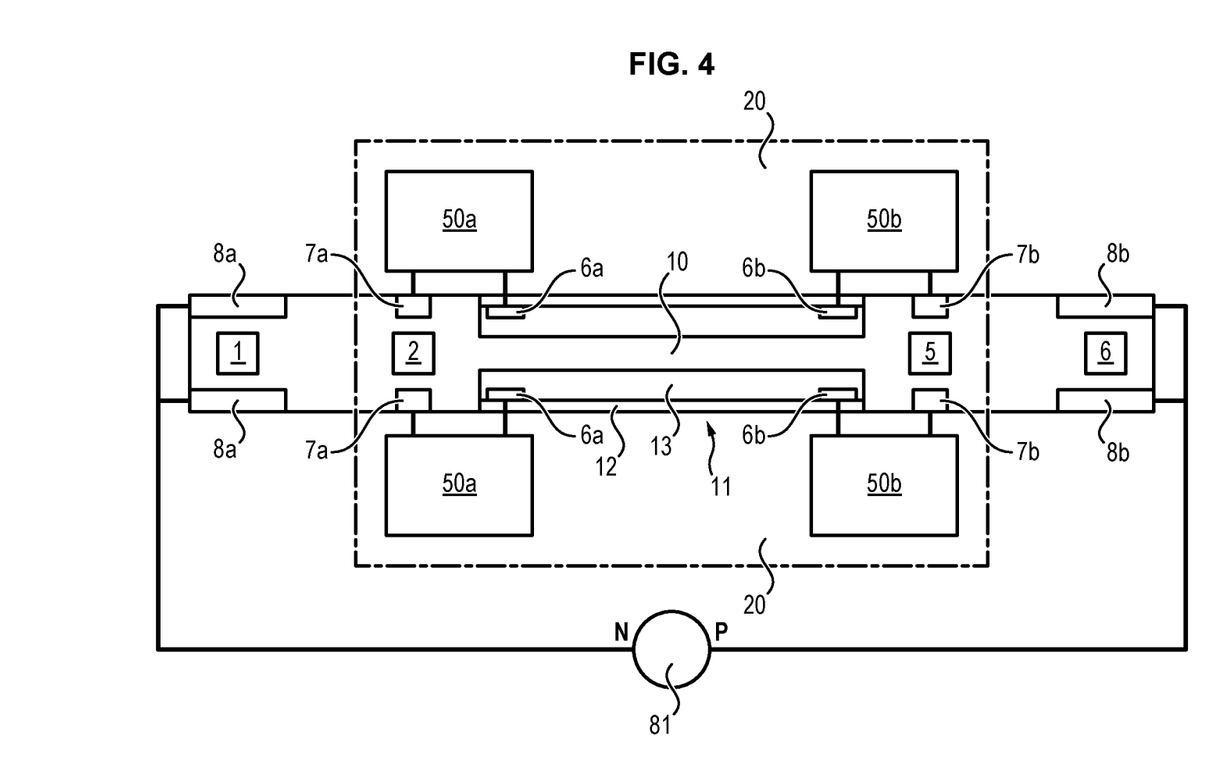
FIG. 4 is a schematic representation of the separation channel and connections intended to be connected to the monitor circuit.

The device further comprises upstream 50a and downstream 50b monitor circuits, each of the reference electrodes 7a, 7b being connected to one of the control electrodes 6a, 6b through a monitor circuit 50a or 50b.

Each of the monitor circuits 50a and 50b is powered by a high voltage power 55.

The upstream control electrode 6a is connected by an upstream monitor circuit 50a to the upstream reference electrode 7a, whereas the downstream control electrode 6b is connected by a downstream monitor circuit 50b to the downstream reference electrode 7b.

The monitor circuits 50a and 50b adjust the potential of the control electrodes 6a, 6b as a function of the electrolyte potential measured by the reference electrodes 7a, 7b, such that the polarisable surface 11 remains in its polarisability window.

The polarisability window of a polarisable surface is the potential range in which the electrode, in the presence of the solvent and the supporting or buffer electrolyte, yields no charge transfer current (or faradic current) at the electrode/solution interface, and regardless the potential applied.

The field is limited by two potential values making up the "solvent wall", that is on the anodic side, solvent oxidation, and on the cathodic side, solvent reduction. In the case of an aqueous solvent such as a biological buffer, the field of zero faradic current is limited by the oxidation of water into $O_2$ and the reduction of water or protons into $H_2$. In the case of concentrated KCl solutions, the oxidation of chloride ions into $Cl_2$ can limit the polarisability field on the anodic side. In the case of an insulating sub-layer 12 of amorphous silicon carbide a-SiC, the polarisability window of the polarisable surface 11 of nitrogen carbon CNx is 4V, that is a potential field between –2V and +2V.

The electrophoresis potential in the separation channel 10 is directly measured by the reference electrodes 7a, 7b, which limits the potential deviations between the electrolyte and the polarisable surface 11 and thus the leakage currents between the polarisable surface 11 and the longitudinal field electrodes 8a, 8b.

Figure 5:
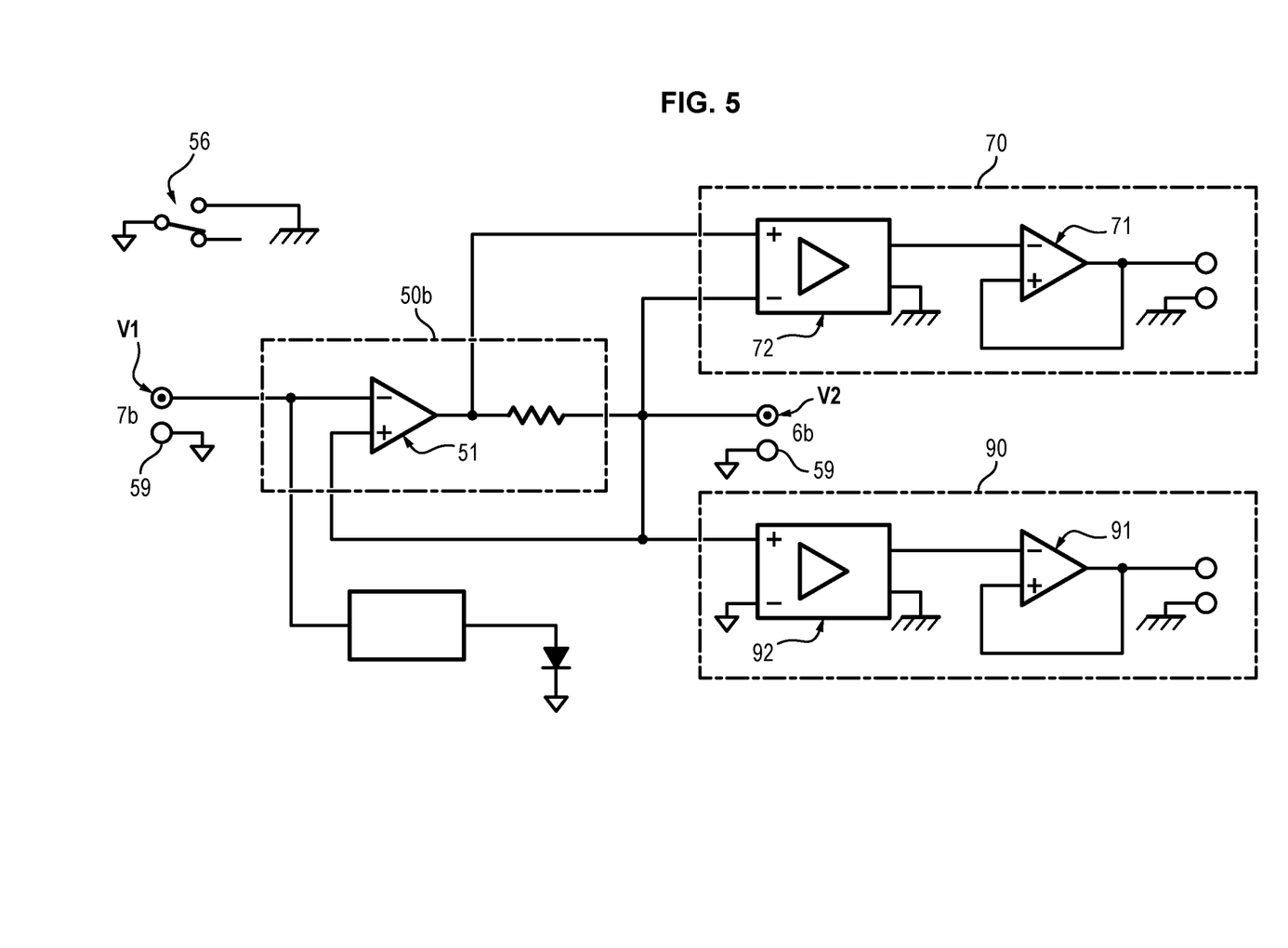
FIG. 5 is a schematic representation of an exemplary mains-operated monitor circuit.

The difficulty in measuring the potential between the electrolyte and the polarisable surface 11 resides in that a potential difference the common mode voltage of which is higher than the power voltage of the operational amplifiers making up the monitor circuit 50b should be measured.

Indeed, during an electrophoresis measurement, the common mode voltage at the downstream control electrode 7b is in the order of 10 to 100 Volts, whereas the power voltage of the operational amplifiers is in the order of –2 to 2 Volts. The operational amplifiers cannot support such a common mode voltage.

The downstream mains-operated monitor circuit 50b is described in further detail below in reference to FIG. 5.

To solve this difficulty, the downstream monitor circuit 50b connected to the downstream control electrode 6b is referenced to a floating ground 59 itself referenced to the downstream reference electrode 7b (FIG. 5). The upstream monitor circuit 50a connected to the upstream control electrode 6a is in turn referenced to the mains ground.

To that end, the input of the downstream monitor circuit 50b connected to the downstream control electrode 6b is connected to the positive terminal of the high voltage power 55.

Reporting the potential value, measured with respect to a floating ground 59, to a value with respect to the mains ground enables the common mode voltage in the downstream monitor circuit 50b to be limited.

A switch 56 advantageously enables the operating mode of the monitor circuit 50b to be chosen between two operating modes, a first operating mode in which the monitor circuit 50b is referenced to the mains ground, and a second operating mode in which the monitor circuit 50b is referenced to a floating ground 59.

In reference to FIG. 5, the microfluidic analysis device 1 can further include a current measurement circuit 70 and a potential measurement circuit 90.

Current Measurement Circuit 70

The current measurement circuit 70 includes a measurement resistance 72 and an operational amplifier 71 the inverting input of which is connected to the reference electrode 6a or 6b and the non-inverting input of which is connected to the output of the first operational amplifier 51.

A switch enables the measurement resistance value 72 to be selected among 1 kΩ, 10 kΩ, 100 kΩ and 1 MΩ in order to refine the current measurements so as to change the value of the amplification gain of the signal measured.

Potential Measurement Circuit 90

The potential measurement circuit 90 includes an operational amplifier 91 the inverting input of which is connected to the non-inverting input of the first operational amplifier 51 and the non-inverting input of which is connected to the floating ground 59.

The upstream monitor circuit 50a is identical to the same with the only difference that it is connected to the mains ground and not the floating ground 59.

Figure 6:
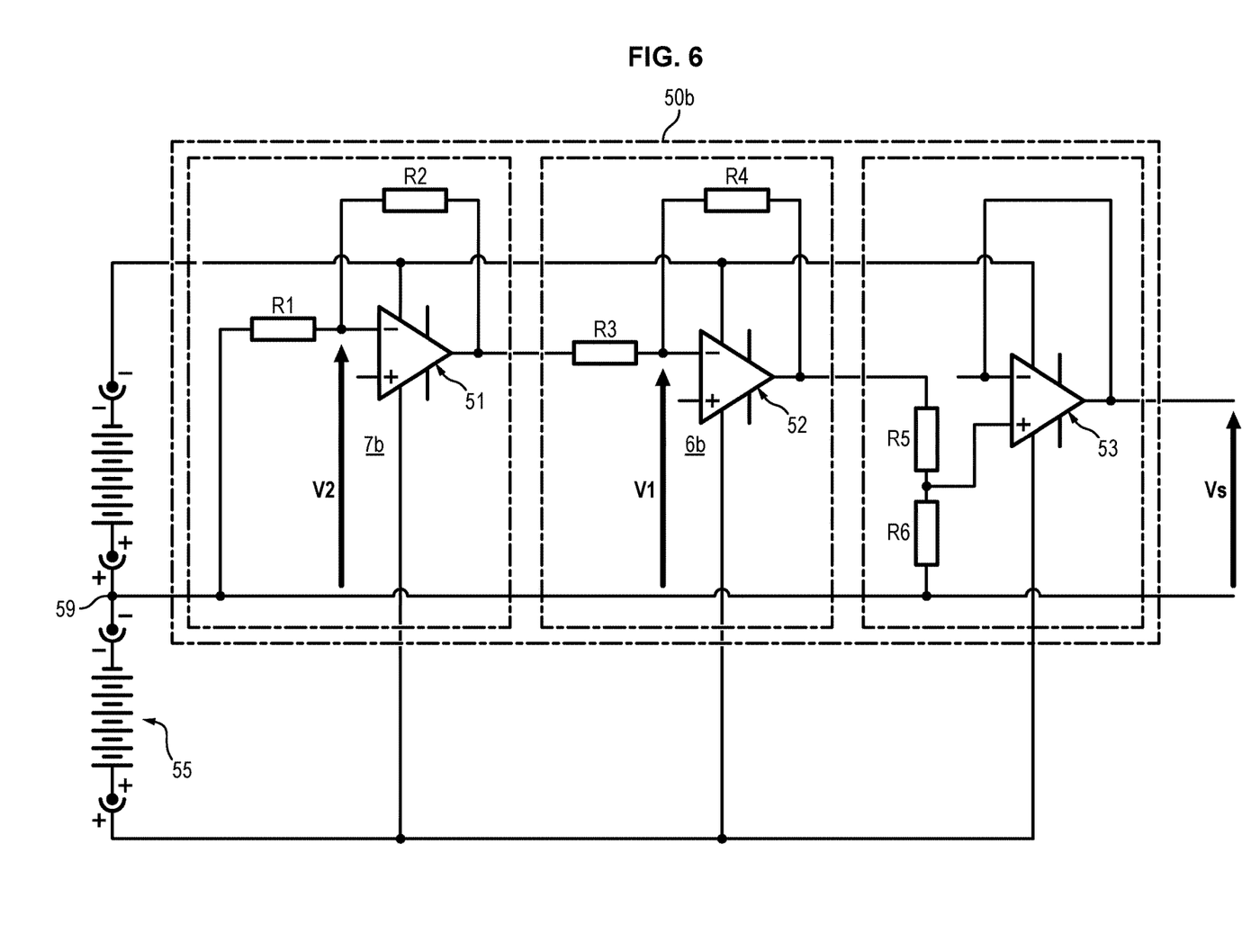
FIG. 6 is a schematic representation of an exemplary battery-operated monitor circuit.

The battery-operated monitor circuit 50b includes a first operational amplifier 51, and a second operational amplifier 52, the first operational amplifier 51 and the second operational amplifier 52 being connected in cascade.

The non-inverting input of the first operational amplifier 51 is connected to the reference electrode 7b. In FIG. 6, the potential of the reference electrode is noted V2.

The reference electrode 7b is connected between the non-inverting input of the first operational amplifier 51 and the floating ground 59.

The inverting input of the first operational amplifier 51 is connected to the floating ground 59 through a first resistance R1.

The output of the first operational amplifier 51 is connected to its inverting input through a second resistance R2.

The output of the first operational amplifier 51 is connected to the inverting input of the second operational amplifier 52 through a third resistance R3.

The output of the second operational amplifier 52 is connected to its inverting input through a fourth resistance R4.

The non-inverting input of the second operational amplifier 52 is connected to the control electrode 6b. In FIG. 6, the potential of the control electrode is noted V1.

The control electrode 6b is connected between the non-inverting input of the second operational amplifier 52 and the floating ground 59.

The transfer function of the first operational amplifier 51 is thus $V2(1+R2/R1)$.

The four resistances R1, R2, R3 and R4 are identical and typically 51 kΩ.

The transfer function of the second operational amplifier 52 is thus 2(V2−V1). A differential amplification at the output of the second operational amplifier 52 is thus achieved with a gain of 2.

In order to have a transfer function with a gain of 1 instead of 2, the battery-operated monitor circuit 50b further includes at the output of the second operational amplifier 52 a voltage divider stage.

The voltage divider stage includes a third operational amplifier 53 the non-inverting input of which is connected to the output of the second operational amplifier 52 through a fifth resistance R5, and to the floating ground 59 through a sixth resistance R6, the fifth resistance R5 and the sixth resistance R6 being equal. In FIG. 6, the potential at the output of the third operational amplifier 53 is noted Vs.

The voltage divider stage thus divides the voltage at the output of the second operational amplifier 52 by a coefficient 2, which enables at the output of the third operational amplifier 53 a measurement of the potential difference between the reference electrode 7b and the control electrode 6b: Vs=(V2−V1) to be obtained.

The upstream monitor circuit 50a is identical to that with this only difference that it is connected to the mains ground and not to the floating ground 59.

The monitor circuit 50b has the advantage to have an infinite theoretical input impedance. The input impedance of the monitor circuit 50b is preferentially higher than 10^10 Ohms and further preferentially higher than 10^12 Ohms, for a longitudinal field voltage in the order of 50 Volts. In practice, the input impedance of the monitor circuit 50b is typically in the order of 3.10^12 Ohms. The monitor circuit 50b thus enables impedance matching needs to be suppressed.

The monitor circuit 50b is an instrumentation amplifier with a high common mode voltage and a high input impedance.

It is to be noted that a conventional follow-up connection could not have been used in place of the monitor circuit 50b, because the operational amplifiers would be destroyed by the common mode voltage level. Indeed, that would become higher than a maximum value allowed by the inputs of these amplifiers.

It is to be noted that a conventional subtractor connection could not have been used either in place of the monitor circuit 50b, because in a conventional subtractor connection, the input impedance is relatively low, which is not compatible with the measurement of low intensity currents with a strong fluctuation in the common mode voltage.

Microfluidic Analysis Method

The microfluidic analysis device 1 can in particular implement the microfluidic analysis method described below, including the following steps:
  injecting an electrolyte containing analytes into the separation channel 10;
  generating a longitudinal field in the separation channel 10;
  polarising the polarisable surface 11 by applying a polarisation voltage across the control electrodes 6a, 6b;
  monitoring the electro-osmotic flow rate in the separation channel 10 by modulating the polarisation voltage across the control electrodes 6a, 6b.

During the step of monitoring the electro-osmotic flux rate in the separation channel 10, the upstream monitor circuit 50a imposes a fixed potential difference between the upstream control electrode 6a and the upstream reference electrode 7a, whereas the downstream monitor circuit 50b imposes a fixed potential difference between the downstream control electrode 6b and the downstream reference electrode 7b. The value of this potential difference is limited by the polarisation range of the upper polarisable layer 11. This value directly monitors the modulation of the surface charge and thus the electro-osmotic flux.

Injecting an Electrolyte Containing Analytes into the Separation Channel 10

The matrix system of solenoid valves 17 controls the introduction of the electrolyte into the fluidic array 100, through a hydrodynamic pressure set by a pressure gauge.

The electrolyte is initially stored in the back-up container 15. After it has passed through the separation channel, the electrolyte is stored in the storage container 16.

The step of injecting an electrolyte containing analytes in the separation channel 10 includes the following sub-steps:
  pre-filling;
  discharging the bubbles;
  hydrodynamic fluxing;
  separation by electrophoresis.

Pre-Filling

The microfluidic analysis device 1 is positioned in a chip holder (not represented). During a pre-filling step, the four tanks 25 and 26 of the microfluidic analysis device 1 are filled with an electrolyte (for example with a syringe). The pre-filling step lasts about 15-20 minutes.

Discharging the Bubbles

During a step of discharging bubbles, possible bubbles present in the fluidic circuit 100 are discharged by alternating the configuration of flowing in a direction in which the back-up container 15 is connected to both left tanks, the configuration of flowing in the other direction in which the back-up container 15 is connected to both right tanks and the balancing configuration in which the back-up container 15 is connected to the four tanks 25a, 25b, 26a and 26b. About one hundred alternating configurations are applied to the microfluidic analysis device 1.

The full disappearance of bubbles is visually checked with an inverted microscope.

Hydrodynamic Fluxing

During a hydrodynamic fluxing step, the four tanks 25a, 25b, 26a and 26b are connected to the back-up container 15 containing the electrolyte and to the empty storage container 16.

A hydrodynamic fluxing is conducted by putting, in a first time, the back-up container 15 containing the electrolyte in connection with one of the upstream tanks and one of the downstream tanks, and then in a second time with the other two tanks.

The hydrodynamic fluxing generates a flow of the electrolyte into the fluidic circuit 100 of the back-up tank 15 up to the storage container 16.

Separation by Electrophoresis

The back-up container 15 is pressurised by a matrix system of solenoid valves 17. The electrolyte initially contained in the back-up container 15 is injected into the upstream secondary tank 25a or 25b so as to flow in the fluidic array 100 up to the downstream tank 26a and 26b before being stored in the storage container 16.

During the step of separation by electrophoresis, the tank 15 is connected to all the secondary tanks 25a, 25b, 26a and 26b so as to achieve pressure balance.

The matrix of solenoid valve is programmed for measuring the surface charge, for example by using particulate anemometry (the rate of the fluorescent micro-beads enables the electro-osmotic flux and thus the surface charge imposed by the fluidic transistor to be known).

Generating a Longitudinal Field in the Separation Channel 10

The longitudinal field in the separation channel 10 is generated by applying a voltage between the longitudinal field electrodes 8a, 8b. The voltage applied between the longitudinal field electrodes 8a, 8b is typically in the order of 50 Volts.

Under the effect of a longitudinal electric field, the particulates and molecules being charged or not move in the electrolyte with a rate defined by all of the field, the mass, an electro-osmosis and the possible particulate charge. This phenomenon is called electrophoresis. The particulate rate in the electrolyte is proportional to the electric field, the proportionality constant being called apparent mobility (sum of the electrophoretic and electro-osmotic mobilities).

Polarising the Polarisable Surface 11

The polarisable surface 11 is polarised by applying a polarising voltage across the control electrodes 6a, 6b.

On the walls of the separation channel 10, a double ion layer formed by a fixed ion layer, corresponding to the surface charge, and a mobile ion layer, corresponding to a diffuse layer in the liquid, is spontaneously formed.

Under the action of the longitudinal electric field, the ions of the mobile layer migrate, causing an overall movement of the electrolyte by viscosity. This is called electro-osmosis.

The electrolyte is moved as a single piece and its rate is proportional to the electric field. The proportionality constant between the fluid rate and the electric field is called electro-osmotic mobility.

The polarisation voltage applied between the control electrodes 6a, 6b and the reference electrodes 7a, 7b enables the charge of the polarisable surface 11 to be modulated.

The polarisation voltage across the control electrodes 6a, 6b is typically in the order of +/−2 volts.

Monitoring the Electro-Osmotic Flux Rate in the Separation Channel 10

The measurement of the potential difference between the reference electrode 7a, 7b and the control electrode 6a, 6b is used to adjust the polarisation voltage applied to the polarisable surface 11, so as to monitor the flux rate in the separation channel 10.

Throughout the step of measuring and monitoring the electro-osmotic flux rate in the separation channel 10, the monitor circuit 50a (respectively 50b) imposes a fixed potential difference between the potential of the control electrode 6a (respectively 6b) and the reference electrode 6a (respectively 6b) such that the polarisable surface 11 remains in its polarisability window.

Imposing a fixed potential difference between the potential of the control electrode 6a (respectively 6b) and the electrolyte enables the leakage currents between the control electrodes 6a (respectively 6b) and the longitudinal field electrodes 8a, 8b to be limited, which are detrimental to monitoring and quality of transport of the analytes during the electrophoretic migration process. These leakage currents become negligible if the control electronics is perfectly adapted and if the polarisable interface material has good electrical properties.

To that end, the monitor circuit 50a (respectively 50b) imposes to the input of the generator 55 the potential of the reference electrode 7a (respectively 7b), whereas the generator 55 imposes a fixed potential difference between the control electrode 6a (respectively 6b) and the reference electrode 7a (respectively 7b). The potential difference between the control electrode 6a (respectively 6b) and the reference electrode 7a (respectively 7b) is typically set to a value between [+2 volts; −2 volts].

The analysis device 1 can in particular be used to modulate the flux in the separation channel 10 in both directions (positive or negative or zero mobility). The analysis device 1 can thus be used as a flow valve or as a pump.

Measuring the Electro-Osmotic Flux Rate in the Separation Channel 10

The concomitant action of the electrophoretic migration (rate of the particles and biomolecules in the electrolyte) and of the electro-osmotic flux (electrolyte rate) ensures the analyte transport in the separation channel 10.

The microfluidic analysis device 100 enables the electro-osmotic flux rate to be measured and monitored in the separation channel 10 in the presence of an electric field through the separation channel 10.

The electro-osmotic flux rate in the separation channel 10 is for example calculated by using the measurement principle of the fluidic Wheatstone bridge described below.

FIG. 2 is an overview of the microfluidic Wheatstone bridge array 100.

The fluidic Wheatstone bridge enables the fluidic resistance of the separation channel 10 to be determined.

The determination of the fluidic resistance of the separation channel 10 where the electrophoresis occurs includes the following steps:
  measuring the four fluidic resistances of the four connecting channels 35a, 36a, 35b, 36b,
  deducing the fluidic resistance of the separation channel 10 where the electrophoresis is conducted from the measurements of the four fluidic resistances of the four connecting channels 35a, 36a, 35b, 36b.

The electro-osmotic flux rate in the separation channel 10 could also be calculated by particle image velocimetry (PIV) or by introducing and detecting a neutral label (for example thiocarbamide or thiourea) which moves with the electro-osmotic flux.

The invention claimed is:

1. A microfluidic analysis device (1) including:
  a substrate (20) wherein a separation channel is arranged, in which an electrolyte flows, a portion of the separation channel (10) being covered with a polarisable surface (11);
  two longitudinal field electrodes (8a, 8b) arranged on either side of the separation channel (10);
  at least one control electrode (6a, 6b) positioned in the separation channel (10), the control electrodes (6a, 6b) being adapted to polarise the polarisable surface (11) so as to monitor the rate of the electro-osmotic flow in the separation channel (10);
  the microfluidic analysis device (1) being characterised in that the polarisable surface (11) includes an insulating sub-layer (12) made of amorphous silicon carbide (a-SiC) and an upper polarisable layer (13) in direct contact with the electrolyte, the control electrodes (6a, 6b) being positioned between the insulating sub-layer (12) of amorphous silicon carbide (SiC) and the upper polarisable layer (13).

2. The microfluidic analysis device (1) according to claim 1, wherein the upper polarisable layer (13) is of nitrogen carbon (CNx).

3. The microfluidic analysis device (1) according to claim 1, further comprising:
  a reference electrode (7a, 7b) adapted to measure the potential of the electrolyte in the separation channel (10);

a monitor circuit (50a, 50b) adapted to adjust the potential of the control electrode (6a, 6b) as a function of the electrolyte potential measured by the reference electrode (7a, 7b), such that the polarisable surface (11) remains in its polarisability window.

4. The microfluidic analysis device (1) according to claim 3, characterised in that the monitor circuit (50a, 50b) is adapted to impose a fixed potential difference between the control electrode (6a, 6b) and the reference electrode (7a, 7b).

5. The microfluidic analysis device (1) according to claim 1, characterised in that it includes at least:
one upstream control electrode (6a) positioned upstream of the channel;
one downstream control electrode (6b) positioned downstream of the channel;
one upstream reference electrode (7a) positioned upstream of the channel;
one downstream reference electrode (7b) positioned downstream of the channel;
the upstream control electrode (6a) is connected by an upstream monitor circuit (50a) to the upstream reference electrode (7a), the downstream control electrode (6b) being connected by a downstream monitor circuit (50b) to the downstream reference electrode (7b), the downstream monitor circuit (50a) being adapted to adjust the potential of the control electrodes (6a, 6b) as a function of the electrolyte potential measured by the reference electrodes (7a, 7b), such that the polarisable surface (11) remains in its polarisability window.

6. The microfluidic analysis device (1) according to claim 5, the downstream monitor circuit (50b) being connected to a floating ground (59) referenced to the downstream reference electrode (7b).

7. The microfluidic analysis device (1) according to claim 6, the downstream monitor circuit (50b) including a first operational amplifier (51), and a second operational amplifier (52), the downstream reference electrode (7b) is connected between the non-inverting input of the first operational amplifier (51) and the floating ground (59), and the downstream control electrode (6b) being connected between the non-inverting input of the second operational amplifier (52) and the floating ground (59).

8. A microfluidic analysis method implemented by a microfluidic analysis device (1) according to claim 1 including the steps of:
injecting an electrolyte containing analytes into the separation channel (10);
generating a longitudinal field in the separation channel (10);
polarising the polarisable surface (11) by applying a polarisation voltage across the control electrodes (6a, 6b) and monitoring the electro-osmotic flow rate in the separation channel (10) by modulating the polarisation voltage across the control electrodes (6a, 6b).

9. The microfluidic analysis method according to claim 8 implemented by a microfluidic analysis device (1), characterised in that during the step of monitoring the electro-osmotic flow rate in the separation channel (10), the polarisation voltage across the control electrodes (6a, 6b) is adjusted as a function of the electrolyte potential measured by the reference electrode (7a, 7b), such that the polarisable surface (11) remains in its polarisability window.

10. The microfluidic analysis method according to claim 9 implemented by a microfluidic analysis device (1), characterised in that during the step of monitoring the electro-osmotic flow rate in the separation channel (10), a fixed potential difference is imposed between the upstream control electrode (6a) and the upstream reference electrode (7a), and between the downstream control electrode (6b) and the downstream reference electrode (7b).

* * * * *